US007455864B2

(12) United States Patent
Heuer et al.

(10) Patent No.: US 7,455,864 B2
(45) Date of Patent: Nov. 25, 2008

(54) MELATONIN-BASED COMPOSITION FOR IMPROVED SLEEP

(75) Inventors: Marvin Heuer, Mississauga (CA); Ken Clement, Mississauga (CA); Shan Chaudhuri, Mississauga (CA); Megan Thomas, Mississauga (CA)

(73) Assignee: Iomedix Development International Srl, Bridgetown (BB)

( * ) Notice: Subject to any disclaimer, the term of this patent is extended or adjusted under 35 U.S.C. 154(b) by 0 days.

(21) Appl. No.: 11/757,744

(22) Filed: Jun. 4, 2007

(65) Prior Publication Data

US 2008/0248103 A1 Oct. 9, 2008

Related U.S. Application Data

(63) Continuation of application No. 11/696,883, filed on Apr. 5, 2007.

(51) Int. Cl.
*A61K 36/53* (2006.01)
*A61K 31/4045* (2006.01)

(52) U.S. Cl. ....................... 424/778; 424/458; 424/469; 424/725; 514/415

(58) Field of Classification Search ....................... None
See application file for complete search history.

(56) References Cited

U.S. PATENT DOCUMENTS

| | | | | |
|---|---|---|---|---|
| 2002/0188025 | A1* | 12/2002 | Ozeki et al. | 514/561 |
| 2003/0077297 | A1* | 4/2003 | Chen et al. | 424/400 |
| 2005/0272690 | A1* | 12/2005 | Cremisi | 514/52 |

FOREIGN PATENT DOCUMENTS

| | | | |
|---|---|---|---|
| CA | 2561616 | A1 | 10/2005 |
| HU | 62477 | T * | 5/1998 |
| WO | 9407487 | A1 | 4/1994 |
| WO | 03015690 | A2 | 2/2003 |

OTHER PUBLICATIONS

Girish et al. (Journal of Ethnopharmacology (2004), vol. 94, pp. 77-83).*

Stoller MK. Economic effects of insomnia. Clin Ther. Sep.-Oct. 1994;16(5):873-97 (Abstract).

Irwin M, et al. Partial night sleep deprivation reduces natural killer and cellular immune responses in humans. FASEB J. Apr. 1996;10(5):643-53.

Karasek M, et al. Melatonin in humans. J Physiol Pharmacol. Nov. 2006;57 Suppl 5:19-39.

Herxheimer A, et al. Melatonin for the prevention and treatment of jet lag. Cochrane Database of Systematic Reviews 2002, Issue 2. Art. No. CD001520. DOI: 10.1002/14651858.CD001520.

Brzezinski A, et al. Effects of exogenous melatonin on sleep: a meta-analysis. Sleep Medicine Reviews. 2005;9:41-50.

Lis-Balchin M, et al. Studies on the mode of action of the essential oil of lavender (*Lavandula angustifolia* P. Miller). Phytother Res. Sep. 1999;13(6):540-2.

Heuberger E, et al. Transdermal absorption of (−)-linalool induces autonomic deactivation but has no impact on ratings of well-being in humans. Neuropsychopharmacology. Oct. 2004;29(10):1925-32.

Fatehi M, et al. Antispasmodic and hypotensive effects of *Ferula asafoetida* gum extract. J Ethnopharmacol. Apr. 2004;91(2-3):321-4 (Abstract).

Saxena RS, et al. Tranquilizing, antihistaminic and purgative activity of Nyctanthes arbor tristis leaf extract. J Ethnopharmacol. Aug. 2002;81(3):321-5 (Abstract).

Soulimani R, et al. Behavioural effects of *Passiflora incarnata* L. and its indole alkaloid and flavonoid derivatives and maltol in the mouse. J Ethnopharmacol. Jun. 1997;57(1):11-20 (Abstract).

Azhondzadeh S, et al. Passionflower in the treatment of generalized anxiety: a pilot double-blind randomized controlled trial with oxazepam. J Clin Pharm Ther. Oct. 2001;26(5):363-7 (Abstract).

Al-Zuhair H, et al. Pharmacological studies of cardamom oil in animals. Pharmacol Res. Jul.-Aug. 1996;34(1-2):79-82.

Lecouvey M, et al. Two-dimensional 1H-NMR and CD structural analysis in a micellar medium of a bovine alphaS1-casein fragment having benzodiazepine-like properties. Eur J Biochem. Sep. 15, 1997;248(3):872-8.

Miclo L, et al. Characterization of alpha-casozepine, a tryptic peptide from bovine alpha(s1)-casein with benzodiazepine-like activity. FASEB J. Aug. 2001;15(10):1780-2.

Yokogoshi H, et al. Reduction effect of theanine on blood pressure and brain 5-hydroxyindoles in spontaneously hypertensive rats. Biosci Biotechnol Biochem. Apr. 1995;59(4):615-8 (Abstract).

Kimura K, et al. L-Theanine reduces psychological and physiological stress responses. Biol Psychol. Jan. 2007;74(1):39-45 (Abstract).

D1: Lee, Beom-Jin et al., "Design and evaluation of an oral controlled release delivery system for melatonin in human subjects." International Journal of Pharmaceutics 1995; 124 p. 119-127.

D2: Lee, Beom-Jin et al. "Formulation and release characteristics of hydroxypropyl methycellulose matrix tablet containing melatonin." Drug Development and Industrial Pharmacy 1999; 25(4) p. 493-501.

International Search Report for PCT/CA2007/000983, International Filing Date: Jun. 4, 2007, Applicant: Iomedix Development International SRL et al.

Iovate Health Sciences Sleep MD, EZ-Swallow Caplets 2006, Retrieved from Internet: URL:http://www.walgreens.com/store/product.jsp?CATID=304747&navAction=jump&navCount=1&skuid=sku2949067&id=prod2950234#, "retrieved on Nov. 6, 2007".

Guillemain J. et al., Effects of neurodepresseurs de l'huile essentielle de *Lavandula angustifolia* Mill., Annales Pharmaceutiques Francaises, 1989, 47:337-343.

PCT International Search Report for PCT/CA2007/000578, International Filing Date Apr. 5, 2007, Applicant: Iomedix Development International Srl et al.

* cited by examiner

*Primary Examiner*—Susan C Hoffman
(74) *Attorney, Agent, or Firm*—Torys LLP

(57) ABSTRACT

A method for improving sleep in an individual comprising the administration of a composition comprising melatonin, lavender flower extract and *Ferula* extract is provided. The composition may be in a layered solid dosage form to provide controlled and sustained release of specific ingredients.

12 Claims, No Drawings

MELATONIN-BASED COMPOSITION FOR IMPROVED SLEEP

RELATED APPLICATIONS

This application is a continuation of the applicant's co-pending U.S. application Ser. No. 11/696,883, filed Apr. 5, 2007 and claims benefit of priority thereto.

FIELD OF THE INVENTION

The present invention is directed towards supplemental compositions containing melatonin and methods for improving sleep and relaxation in an individual.

BACKGROUND OF THE INVENTION

Sleep occupies about one-third of our life and is necessary for mental and physical well-being. It additionally affects mood, behavior and physiology. Sleep and the control of sleep is a complex process involving multiple neuro-chemical pathways and associated brain structures. It is a dynamic process involving a shift in the balance of distinct physiological changes, involving both positive and negative signaling neural signaling. The regulation of sleep in humans is governed by three processes—each influenced by hormonal and environmental factors: a daily sleep-wake cycle influenced by a circadian rhythm (24 hour cycle) tied to light-dark cycles.

The need for sleep is a biological drive similar to thirst or hunger. Interestingly though, the function of sleep is largely unknown, however some evidence indicates that sleep is required for learning. In North America, insomnia is estimated to affect a significant portion of the population every year and is associated with health problems and concomitant economic loss to society (Stoller M K. Economic effects of insomnia. Clin Ther. 1994 September-October;16(5):873-97 Abstract). It is clear that the impairment of sleep is detrimental to one's health. In humans, mild sleep deprivation results in indications of impaired immune system function (Irwin M, McClintick J, Costlow C, Fortner M, White J, Gillin J C. Partial night sleep deprivation reduces natural killer and cellular immune responses in humans. FASEB J. 1996 April;10 (5):643-53.). Prolonged sleep deprivation is even known to result in death. It has been determined by many that an individual can survive longer without food than one can without sleep; thus indicating the importance of sleep.

Strategies to improve sleep are beneficial, not only in terms of physical health, but also in terms of emotional health. Furthermore, reinforcement of sleep of adequate quantity and quality positively impacts most aspect of daily life.

SUMMARY OF THE INVENTION

The foregoing needs and other needs and objectives that will become apparent for the following description are achieved in the present invention, which comprises a supplemental composition comprising an effective amount of melatonin, an effective amount of an extract of lavender and an effective amount of an extract of *Ferula* to improve sleep and relaxation in an individual. The composition may be provided in a multi-compartmentalized capsule-based form to facilitate a controlled and sustained release of specific active ingredients in a specific sequence of release.

DETAILED DESCRIPTION OF THE INVENTION

In the following description, for the purposes of explanations, numerous specific details are set forth in order to provide a thorough understanding of the present invention. It will be apparent, however, to one of ordinary skill in the art that the present invention may be practiced without these specific details.

The present invention is directed towards compositions and methods to improve sleep and relaxation. In an embodiment of the present invention, the composition comprises melatonin, lavender flower powder and *Ferula.*

In another embodiment of the present invention, the composition comprises melatonin, lavender flower powder and *Ferula* in a multi-compartmentalized dosage form comprised of a plurality individual capsule-based compartments wherein each of the capsule-based compartments contains specific ingredients to a provide specific and controlled release of specific active ingredients in a predetermined sequence to facilitate the quality of sleep and relaxation in a mammal.

In another embodiment of the present invention, the composition comprises melatonin, lavender flower powder and *Ferula* in a multi-compartmentalized dosage form comprised of a plurality of beadlets contained in a capsule dosage from wherein each of the beadlets contains specific ingredients to a provide specific and controlled release of specific active ingredients in a predetermined sequence to facilitate the quality of sleep and relaxation in a mammal.

It is herein understood that improvements in sleep may be both of a quantitative nature, e.g. increased length of sleep, decreased time of sleep onset, and of a qualitative nature e.g. deeper, more restful undisturbed and following an ideal pattern through the four known stages of sleep. It is further understood that improvements in sleep may also be both direct and indirect. For example, sleep will be directly improved by the administration of a substance which is known to reduce time to sleep onset. Sleep may be indirectly improved, for example, by the administration of a substance which is known to result in feelings of relaxation and calmness.

As used herein the term 'unmodified-release' format is understood to be defined as pertaining to the dissolution and bioavailability profile of an ingested dietary ingredient wherein no additional modifications, be it chemical or physical, have been made to the ingredient with the specific intent to alter the dissolution or bioavailability profile from that of ingredient in a naturally occurring form. It is also understood that unmodified-release is, essentially, immediate-release of active ingredients. This is further understood to be traditional- or conventional-release format where no slow-, delayed- or extended-release effect is incorporated.

As used herein the term 'controlled-release' format is understood to be defined as a formulation of active ingredients and appropriate excipients in a specific format to facilitate a controlled- or non-immediate-release of active ingredients. The components of a controlled-release format may have been subjected to additional modifications, be it chemical or physical, with the specific intent to alter the dissolution or bioavailability profile from that of ingredient in a naturally occurring form.

As used herein the term 'slow-release' format is understood to be defined as a controlled-release format wherein the release of active ingredients are delayed for a period of time or gradually released over an extended period of time. This is accomplished through the use of specific excipients and may include structural features designed to facilitate controlled-release. It is further understood that a slow-release format releases active ingredients at a rate slower than immediate-release.

As used herein the term 'delayed-release' format is understood to be defined essentially as a controlled-release format wherein the components of the delayed-release format have undergone specific modifications, be it physical or chemical, to facilitate the release of active ingredients at a specific time after ingestion. It is further understood that delayed-release formats, release active ingredients at a period of time later than unmodified release.

As used herein the term 'quick-release' format is understood to be defined essentially as 'unmodified-release', as defined above. However, the term 'quick-release' may further include components having modifications, chemical or physical, to enhance the rate of dissolution or bioavailability of active ingredients.

Melatonin

Melatonin is a hormone produced by the pineal gland and is derived from the amino acid tryptophan. While possibly being involved in multiple biological processes, melatonin has largely been studied for its involvement in sleep regulation (Karasek M, Winczyk K. Melatonin in humans. J Physiol Pharmacol. 2006 November;57 Suppl 5:19-39) with respect to the circadian rhythm cycle of an individual. Levels of melatonin cycle in the body based on lighting conditions—i.e. low melatonin levels during the day, higher levels at night. Typically, melatonin levels peak in the middle of the night and diminish thereafter. Melatonin has further been explored as a method to treat sleep disorders such as insomnia and 'jet lag' due to its apparent involvement the regulation of circadian rhythms. Melatonin supplementation in humans has been found to be efficacious for treating jet lag (Herxheimer A, Petrie K J. Melatonin for the prevention and treatment of jet lag. Cochrane Database of Systematic Reviews 2002, Issue 2. Art. No.: CD001520. DOI: 10.1002/14651858.CD001520) as well as hastening the onset of sleep (Brzezinski A, Vangel M, Wurtman R, Norrie G, Zhdanova I, Ben-Shushan A, Ford I. 2005. Effects of exogenous melatonin on sleep: a meta-analysis. Sleep Medicine Reviews 9:41-50).

In a preferred embodiment of the present invention which is set forth in greater detail in the example below, the composition includes melatonin to improve sleep onset and sleep quality. A serving of the supplemental composition includes from about 0.0001 g to about 0.1000 g of melatonin. For the purposes of the present invention, said melatonin is provided in three distinct formats wherein each of said formats provided is designed to have different rate of release. A first dosage format comprises from about 0.0001 g to about 0.005 g of melatonin in a quick-release format. About 0.0030 g of melatonin in said first dosage format is preferably provided in a serving. A second dosage format of melatonin comprising a slow-release technology in the present invention comprises from about 0.0001 g to about 0.005 g of melatonin. About 0.0020 g of melatonin in said second dosage format is preferably provided in a serving. A third dosage format of said melatonin of the present invention comprises from about 0.0010 g to about 0.0100 g of melatonin in an unmodified release format. The preferred dosage of said third format comprises about 0.0050 g of melatonin.

Lavender (*Lavandula Officinalis*)

Oil from the lavender plant is commonly used in aromatherapy for relaxation. The mild sedative effects of lavender have been demonstrated in animals and humans (Lis-Balchin M, Hart S. Studies on the mode of action of the essential oil of lavender (*Lavandula angustifolia* P. Miller). Phytother Res. 1999 September; 13(6):540-2). Transdermal absorption of the main constituent of lavender oil, linalool, has been shown to reduce blood pressure and skin temperature in humans, evidencing a relaxing effect (Heuberger E, Redhammer S, Buchbauer G. Transdermal absorption of (−)-linalool induces autonomic deactivation but has no impact on ratings of well-being in humans. Neuropsychopharmacology. 2004 October; 29(10):1925-32).

In a preferred embodiment of the present invention which is set forth in greater detail in the example below, the composition includes lavender flower powder to promote a feeling of relaxation. A serving of the supplemental composition includes from about 0.0010 g to about 0.0100 g of lavender flower powder. The preferred dosage of lavender flower powder in the present invention comprises about 0.0050 g. per serving.

*Ferula*

*Ferula* is a genus of herbaceous perennial plant that has scented flowers and is native to the Mediterranean region east to central Asia, mostly growing in arid climates. *Ferula* extracts have demonstrated relaxant effects (Fatehi M, Farifteh F, Fatehi-Hassanabad Z. Antispasmodic and hypotensive effects of *Ferula asafoetida* gum extract. J Ethnopharmacol. 2004 April;91(2-3):321-4 Abstract).

In an embodiment of the present invention which is set forth in greater detail in the example below, the composition includes *Ferula* to reduce anxiety. A serving of the supplemental composition includes from about 0.0001 g to about 0.0050 g of *Ferula*. The preferred dosage of *Ferula* in the present invention comprises about 0.0010 g per serving.

*Nyctanthes*

Is a genus of plants of the family *Oleaceae,* native to South East Asia. It contains two species, the most well-known species is the Night-Flowering Jasmine (*Nyctanthes arbortirstis*) and it is sometimes called the tree of sorrow because the flowers lose their brightness during daytime. *Nyctanthes* extracts have been shown to have tranquilizing effects (Saxena R S, Gupta B, Lata S. Tranquilizing, antihistaminic and purgative activity of *Nyctanthes* arbor tristis leaf extract. J Ethnopharmacol. 2002 August;81(3):321-5 Abstract).

In a preferred embodiment of the present invention which is set forth in greater detail in the example below, the composition includes *Nyctanthes* to promote feelings of tranquility. A serving of the supplemental composition includes from about 0.0001 g to about 0.0050 g of *Nyctanthes*. The preferred dosage of *Nyctanthes* in the present invention comprises about 0.0010 g per serving.

Passion Flower

Passion flower has been used traditionally for relaxation and as a sleep-aid and treatment for anxiety. Specific flavonoids contained in Passion flower have been shown to have sedative properties. Furthermore, Passion flower extract has been noted to reduce anxiety and induce sleep in mice (Soulimani R, Younos C, Jarmouni S, Bousta D, Misslin R, Mortier F. Behavioural effects of Passiflora incarnata L. and its indole alkaloid and flavonoid derivatives and maltol in the mouse. J Ethnopharmacol. 1997 June;57(1):11-20 Abstract). Clinical trials in humans have demonstrated that Passion flower is effective in the treatment of anxiety (Akhondzadeh S, Naghavi H R, Vazirian M, Shayeganpour A, Rashidi H, Khani M. Passionflower in the treatment of generalized anxiety: a pilot double-blind randomized controlled trial with oxazepam. J Clin Pharm Ther. 2001 October; 26(5):363-7 Abstract).

In an embodiment of the present invention which is set forth in greater detail in the example below, the composition includes an extract of Passion flower to promote feelings of relaxation and calmness and to induce sleep. A serving of the supplemental composition includes from about 0.0001 g to about 0.0050 g of an extract of Passion flower. The preferred dosage of an extract of Passion flower in the present invention comprises about 0.002 g per serving.

*Elettaria Cardamom*

One of 2 species of the Indian spice cardamom, *Elettaria cardamom* is used in Traditional Chinese Medicine for a variety of medicinal purposes. Animal studies show that cardamom extract has antispasmodic relaxant effects (al-Zuhair H, el-Sayeh B, Ameen H A, al-Shoora H. Pharmacological studies of cardamom oil in animals. Pharmacol Res. 1996 July-August; 34(1-2):79-82).

In an embodiment of the present invention which is set forth in greater detail in the example below, the composition includes *Elettaria cardamom* to promote feelings of relaxation. A serving of the supplemental composition includes from about 0.0001 g to about 0.0050 g of *Elettaria cardamom.* The preferred dosage of *Elettaria cardamom* in the present invention comprises about 0.0010 g per serving.

Lactium®

Lactium® is a hydrolyzed milk peptide that has been used in stress management in adult females, and has demonstrated a protective effect on sleep during periods of mild chronic stress in mice. The action is likely mediated via binding of this specific peptide, having the amino acid sequence of [91]Typ-Leu-Gly-Tyr-Leu-Glu-Gln-Leu-Leu-Arg[100] in a benzodiazepine-like fashion (Lecouvey M, Frochot C, Miclo L, Orlewski P, Driou A. Linden G. Gaillard J L, Marraud M, Cung M T, Vanderesse R, Two-dimensional 1H-NMR and CD structural analysis in a micellar medium of a bovine alphaS1-casein fragment having benzodiazepine-like properties. Eur J Biochem. 1997 September 15;248(3):872-8), to Gamma Aminobutyric Acid (GABA) receptors (Miclo L, Perrin E, Driou A, Papadopoulos V, Boujrad N, Vanderesse R, Boudier J F, Desor D, Linden G, Gaillard J L. Characterization of alpha-casozepine, a tryptic peptide from bovine alpha(s1)-casein with benzodiazepine-like activity. FASEB J. 2001 August; 15(10):1780-2). The neurotransmitter GABA, is the primary inhibitory neurotransmitter and one of its effects is to induce sleep. Signaling through the GABA-receptor changes the electrochemical gradient of the neuron, leading to activity inhibition. Benzodiazepines are thought to act via interaction with the GABA receptor; thus enhancing the inhibitory effects of GABA. As such, benzodiazepines are a widely used class of drugs primarily used as tranquilizers, muscle-relaxants, hypnotics or sedatives.

In an embodiment of the present invention which is set forth in greater detail in the example below, the composition includes Lactium® to promote feelings of relaxation and to induce sleep. A serving of the supplemental composition includes from about 0.0001 g to about 0.0050 g of Lactium®. The preferred dosage of Lactium® in the present invention comprises about 0.0010 g per serving.

Theanine

Theanine, also known as γ-glutamethylethylamide and N-ethyl-L-glutamine, is an amino acid found in green tea. It is however distinct from the polyphenols and catechins which are typically associated with the beneficial effects of green tea. While catechins are generally associated with antioxidant activities, theanine is associated with anti-stress. In hypertensive rats, theanine lowers blood pressure (Yokogoshi H, Kato Y, Sagesaka Y M, Takihara-Matsuura T, Kakuda T, Takeuchi N. Reduction effect of theanine on blood pressure and brain 5-hydroxyindoles in spontaneously hypertensive rats. Biosci Biotechnol Biochem. 1995 April;59(4):615-8 Abstract). Moreover, oral theanine administration to humans has additionally been shown to reduce stress (Kimura K, Ozeki M, Juneja L R, Ohira H. L-Theanine reduces psychological and physiological stress responses. Biol Psychol. 2007 January; 74(1):39-45 Abstract).

In an embodiment of the present invention which is set forth in greater detail in the example below, the composition includes theanine to reduce stress. A serving of the supplemental composition includes from about 0.010 g to about 0.100 g of theanine. The preferred dosage of theanine in the present invention comprises about 0.052 g per serving.

*Gardenia Gummifera*

*Gardenia gummifera* is a plant indigenous to China where it is commonly called zhi zhi. In traditional medicine this plant has been purported to have actions which include calming, cooling blood, and clearing away heat. These attribute are desirable for improving the quality of sleep in an individual following ingestion.

In an embodiment of the present invention which is set forth in greater detail in the example below, the composition includes *Gardenia gummifera* to promote feelings of relaxation. A serving of the supplemental composition includes from about 0.0001 g to about 0.0050 g of *Gardenia gummifera* The preferred dosage of *Gardenia gummifera* in the present invention comprises about 0.0010 g per serving.

*Marjoram*

*Marjoram* is an herb commonly used in aromatherapy and is known for its soothing effects and is additionally purported to relieve anxiety.

In an embodiment of the present invention which is set forth in greater detail in the example below, the composition includes *Marjoram* to reduce anxiety and promote feelings of relaxation. A serving of the supplemental composition includes from about 0.0001 g to about 0.0050 g of *Marjoram.* The preferred dosage of *Marjoram* in the present invention comprises about 0.0010 g per serving.

The present invention may additionally further comprise between from about 0.0001 g and about 0.0050 g of sweet violet per serving. The preferred dosage of Sweet violet in the present invention comprises about 0.0010 g per serving.

The present invention may additionally further comprise between from about 0.000001 g and about 0.00001 g of Vitamin B12 per serving. The preferred dosage of Vitamin B12 in the present invention comprises about 0.000006 g per serving.

In a preferred embodiment of the present invention, the composition is comprised of melatonin, lavender flower extract and *Ferula* extract.

In another embodiment of the present invention, the composition is comprised of melatonin, lavender flower extract, *Ferula* and one or more of the following: Passion flower extract, *Nyctanthes, Elettaria cardamom,* Lactium®, Theanine, *Gardenia gummifera* and *Marjoram.*

Optionally, various embodiments of the present invention comprise Sweet violet and Vitamin B12.

Not wishing to be bound by theory, it is believed that the individual components of the present invention in all of its embodiments will act to advantageously improve sleep by the combined and synergistic effects of directly promoting sleep onset and maintenance and indirectly by promoting feelings conducive to sleep such as relaxation and calmness. Furthermore, the various time-release formats and specific dosages thereof of specific ingredient comprising the compositions disclosed herein contribute to an effective dosing regime over the duration of an individual's night sleep. The respective amounts of said ingredients in the various time-release formats are herein understood by the inventors provide an effective about of said ingredient at points during one's sleep when they are in need thereof.

According to various embodiments of the present invention, the supplemental composition may be consumed in any form. For instance, the dosage form of the nutritional supplement may be provided as, e.g., a powder beverage mix, a liquid beverage, a ready-to-eat bar or drink product, a capsule, a liquid capsule, a tablet, a caplet, or as a dietary gel. The preferred dosage form of the present invention is that of a dietary gel.

It is know in the art that the various release formats may be achieved through the use of specific excipients and specific combinations of excipients. Furthermore, it is known that a single oral solid dosage format may be produced that provides combinations of release formats. Such formats may be described as having multi-phasic release properties. Furthermore, each specific release format contained in such a multi-phasic release format may be physically separated into distinct compartments.

Such multi-phasic, multi-compartment formats may contain a homogeneous mixture of ingredients separated into distinct compartments, each with a distinct release format, to achieve a complex controlled-release of all ingredients contained in the multi-phasic, multi-compartment format.

Alternatively, such multi-phasic, multi-compartment formats may contain specific different ingredients in different compartments, each with a distinct release format, to achieve a complex controlled-release of specific ingredients at distinct times. The specific ingredients of specific compartments may be in a particular form e.g. solid, powder, liquid, gel, beadlet, as dictated by the nature of the specific ingredients or by the desired release format.

Advantageously, in a preferred embodiment, the present invention may be provided in a multi-phasic, multi-compartment format that facilitates the specific release of particular ingredients in such a way that the desired beneficial effect is achieved. By way of example, specific components of the present invention directed at promoting the onset of sleep may be contained in a specific compartment of a multi-phasic, multi-compartment format for immediate- or quick-release to quickly encourage sleep in an individual. Other specific components of the present invention directed at promoting the maintenance of sleep may be contained in a specific different compartment of a multi-phasic, multi-compartment format for slow- or delayed-release to encourage the maintenance of sleep in an individual. In this way, the specific ingredients of the various embodiments of the present invention may be made bioavailable at a specific predetermined time-frame to maximize beneficial effects based on mechanism of action or intended use for improving sleep and relaxation in an individual.

According to a preferred embodiment of the present invention, the supplemental composition may be provided in a dietary gel format. The dietary gel is comprised of ingredients wherein like ingredient may be in various time-release formats; a quick-release format, a slow-release format and unmodified release format. In such a form each time-release format will provide unique release characteristics such that a predetermined amount of a specific ingredient is available within an individual following ingestion at given time points. In this way a controlled release of the composition can be achieved to maintain effective amounts specific ingredients at time points wherein said ingredients would provide the most effective benefit to improve the quality sleep in an individual.

The dosage form of the supplemental composition may be provided in accordance with customary processing techniques for herbal and nutritional supplements in any of the forms mentioned above. Additionally, the supplemental composition set forth in the example embodiment herein may contain any appropriate number and type of excipients, as is well known in the art.

Furthermore, by way of ingestion of the composition of the present invention, a method for improving the onset of sleep and improvement of sleep quality is provided.

The present nutritional composition or those similarly envisioned by one of skill in the art, may be utilized in methods to improve the quality of sleep in an individual.

Although the following examples illustrate the practice of the present invention in two of its compositional example embodiments the examples should not be construed as limiting the scope of the invention. Other embodiments will be apparent to one of skill in the art from consideration of the specifications and example.

EXAMPLES

Example 1

A nutritional supplement to help promote quality sleep for use immediately prior to bedtime. A serving of the nutritional supplement contains the following:

About 0.0050 g of unmodified-release melatonin, about 0.0030 g of quick-release melatonin, about 0.0020 g of slow-release melatonin, about 0.0050 g of lavender flower powder, about 0.0010 g of *Ferula narthex,* about 0.0020 g of Passion flower extract, about 0.0010 g of *Elettaria cardamom,* about 0.0010 g of Lactium®, about 0.0520 g of Theanine, about 0.0010 g of *Gardenia gummifera* and about 0.0010 g of *Marjoram.*

Example 2

A nutritional supplement to help promote quality sleep for use immediately prior to bedtime. A serving of the nutritional supplement contains the following:

About 0.0050 g of unmodified-release melatonin, about 0.0030 g of quick-release melatonin, about 0.0020 g of slow-release melatonin, about 0.0050 g of lavender flower powder, about 0.0010 g of *Ferula narthex,* about 0.0010 g of *Nyctanthes,* about 0.0020 g of Passion flower extract, about 0.0010 g of *Elettaria cardamom,* about 0.0010 g of Lactium®, about 0.0520 g of Theanine, about 0.0010 g of *Gardenia gummifera,* about 0.0010 g of *Marjoram,* about 0.0010 g of Sweet violet, and about 0.000006 g of Vitamin B12.

Extensions and Alternatives

In the foregoing specification, the invention has been described with a specific embodiment thereof, however, it will be evident that various modifications and changes may be made thereto without departing from the broader spirit and scope of the invention.

What is claimed:

1. A sleep aid composition comprising;

a capsule containing a liquid and a plurality of beadlets containing an extract of *Lavandula officinalis* flower suspended therein; said liquid comprising at least a first dosage of melatonin; and said plurality of beadlets comprising at least a second dosage of melatonin wherein said capsule provides a multi-phasic controlled-release of the first dosage of melatonin in relation to the release of the second dosage of melatonin.

2. The sleep aid composition of claim 1 wherein the liquid is provided as a gel.

3. The sleep aid composition of claim 1 wherein the plurality of beadlets further comprise an extract of *Ferula*.

4. The sleep aid composition of claim 3 wherein the extract of *Ferula* is provided as *Ferula narthex* powder.

5. The sleep aid composition of claim 1 wherein the extract of *Lavandula officinalis* flower is provided as *Lavandula officinalis* flower powder.

6. The sleep aid composition of claim 3 wherein the beadlets further comprise Theanine.

7. A method for improving sleep comprising the administration to an individual a sleep aid composition comprising;

a capsule containing a liquid and a plurality of beadlets containing an extract of *Lavandula officinalis* flower suspended therein; said liquid comprising at least a first dosage of melatonin; and said plurality of beadlets comprising at least a second dosage of melatonin wherein said capsule provides a multi-phasic controlled-release of the first dosage of melatonin in relation to the release of the second dosage of melatonin.

8. The method of claim 7 wherein the liquid is provided as a gel.

9. The method of claim 7 wherein the plurality of beadlets further comprise an extract of *Ferula*.

10. The method of claim 9 wherein the extract of *Ferula* is provided as *Ferula narthex* powder.

11. The method of claim 7 wherein the extract of *Lavandula officinalis* flower is provided as *Lavandula officinalis* flower powder.

12. The method of claim 9 wherein the beadlets further comprise

Theanine.

* * * * *